United States Patent
Lutze et al.

(10) Patent No.: US 7,077,851 B2
(45) Date of Patent: Jul. 18, 2006

(54) ANEURYSM CLIP

(75) Inventors: Theodor Lutze, Balgheim (DE);
Manfred Fischer, Tuttlingen (DE);
Thomas A. Kopitnik, Jr., Dallas, TX (US)

(73) Assignee: Aesculap AG & Co. KG, Tuttlingen (DE)

( * ) Notice: Subject to any disclaimer, the term of this patent is extended or adjusted under 35 U.S.C. 154(b) by 155 days.

(21) Appl. No.: 10/402,318

(22) Filed: Mar. 28, 2003

(65) Prior Publication Data

US 2003/0199888 A1 Oct. 23, 2003

Related U.S. Application Data

(63) Continuation of application No. PCT/US00/41200, filed on Oct. 17, 2000.

(51) Int. Cl.
*A61B 17/08* (2006.01)
(52) U.S. Cl. .................. 606/158; 606/139; 606/142; 606/157; 24/327; 24/571; 24/521; 24/556; 24/547
(58) Field of Classification Search ............... 606/157, 606/158, 151, 207, 142, 143; 24/546, 547, 24/548, 30.5 R, 327, 556, 571, 521
See application file for complete search history.

(56) References Cited

U.S. PATENT DOCUMENTS

| | | | |
|---|---|---|---|
| 825,829 A * | 7/1906 | Heath | 606/135 |
| 1,452,372 A * | 4/1923 | Gomez | 606/217 |
| 1,560,687 A * | 11/1925 | Hauber | 606/120 |
| 1,837,277 A * | 12/1931 | Lund | 606/110 |
| 3,209,753 A * | 10/1965 | Hawkins et al. | 606/207 |
| 3,802,437 A | 4/1974 | Kees, Jr. | |
| 3,827,438 A * | 8/1974 | Kees | 606/158 |
| 4,024,868 A * | 5/1977 | Williams | 606/158 |
| 4,192,315 A * | 3/1980 | Hilzinger et al. | 606/158 |
| 4,360,023 A * | 11/1982 | Sugita et al. | 606/158 |
| 4,605,002 A * | 8/1986 | Rebuffat | 606/148 |
| 4,706,668 A * | 11/1987 | Backer | 606/142 |
| 4,765,335 A * | 8/1988 | Schmidt et al. | 606/158 |
| 4,777,950 A * | 10/1988 | Kees, Jr. | 606/158 |
| 4,796,625 A * | 1/1989 | Kees, Jr. | 606/158 |
| 4,827,930 A * | 5/1989 | Kees, Jr. | 606/142 |

(Continued)

FOREIGN PATENT DOCUMENTS

DE 33 02 707 12/1983

(Continued)

*Primary Examiner*—Glenn K. Dawson
*Assistant Examiner*—Darwin P. Erezo
(74) *Attorney, Agent, or Firm*—Lipsitz & McAllister, LLC

(57) ABSTRACT

An aneurysm clip (1) is provided with two arms (2, 3) which are resiliently pivotable towards each other and carry at their free end clamping bars (12, 13) which are resiliently clamped against each other by the spring force of the arms, with outwardly curved sections of the arms adjoining the clamping bars and jointly forming a receiving space (10) for a vessel (11). In order to improve the safety of the application and the possibility of varying the application of the aneurysm clip, the clamping bars protrude from the arms towards both sides and thereby project laterally on both sides over the width of the arms in the outwardly curved sections.

24 Claims, 5 Drawing Sheets

U.S. PATENT DOCUMENTS

Figure 7:
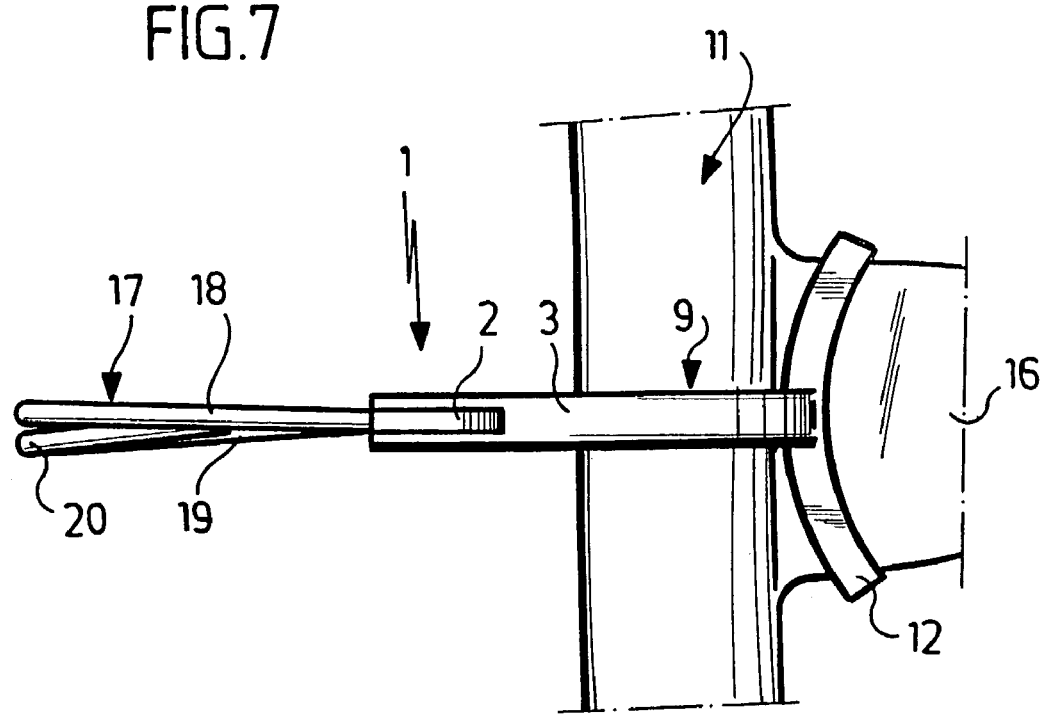

| | | | | |
|---|---|---|---|---|
| 4,943,298 A | * | 7/1990 | Fujita et al. | 606/158 |
| 4,961,743 A | * | 10/1990 | Kees, Jr. et al. | 606/158 |
| 5,019,092 A | | 5/1991 | Klintmalm | |
| 5,053,045 A | * | 10/1991 | Schmidt et al. | 606/157 |
| 5,312,426 A | * | 5/1994 | Segawa et al. | 606/158 |
| 5,457,858 A | * | 10/1995 | Lin | 24/511 |
| 5,593,414 A | * | 1/1997 | Shipp et al. | 606/142 |
| 5,621,955 A | * | 4/1997 | Schmid et al. | 24/511 |
| 5,683,405 A | * | 11/1997 | Yacoubian et al. | 606/158 |
| 6,251,117 B1 | * | 6/2001 | Kringel et al. | 606/158 |
| 6,293,954 B1 | * | 9/2001 | Fogarty et al. | 606/151 |
| 6,350,269 B1 | * | 2/2002 | Shipp et al. | 606/143 |
| 6,652,545 B1 | * | 11/2003 | Shipp et al. | 606/157 |

FOREIGN PATENT DOCUMENTS

| | | |
|---|---|---|
| EP | 0 346 084 | 12/1989 |
| GB | 267326 * | 3/1926 |
| WO | 98/18389 | 5/1998 |

* cited by examiner

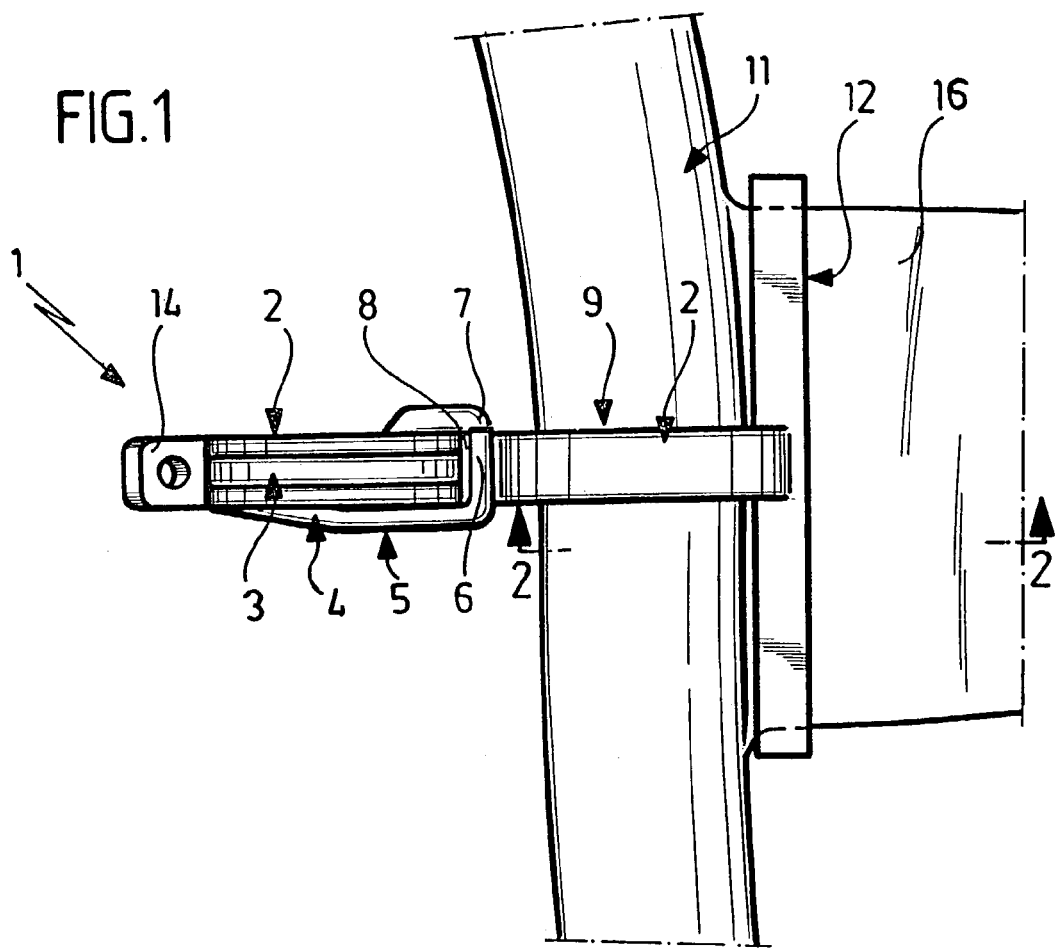
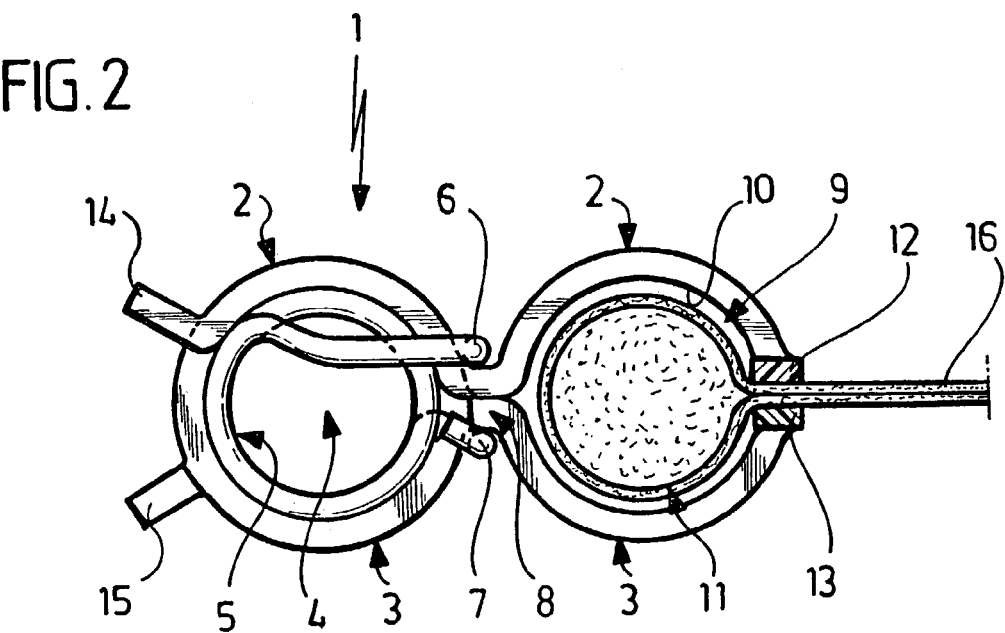

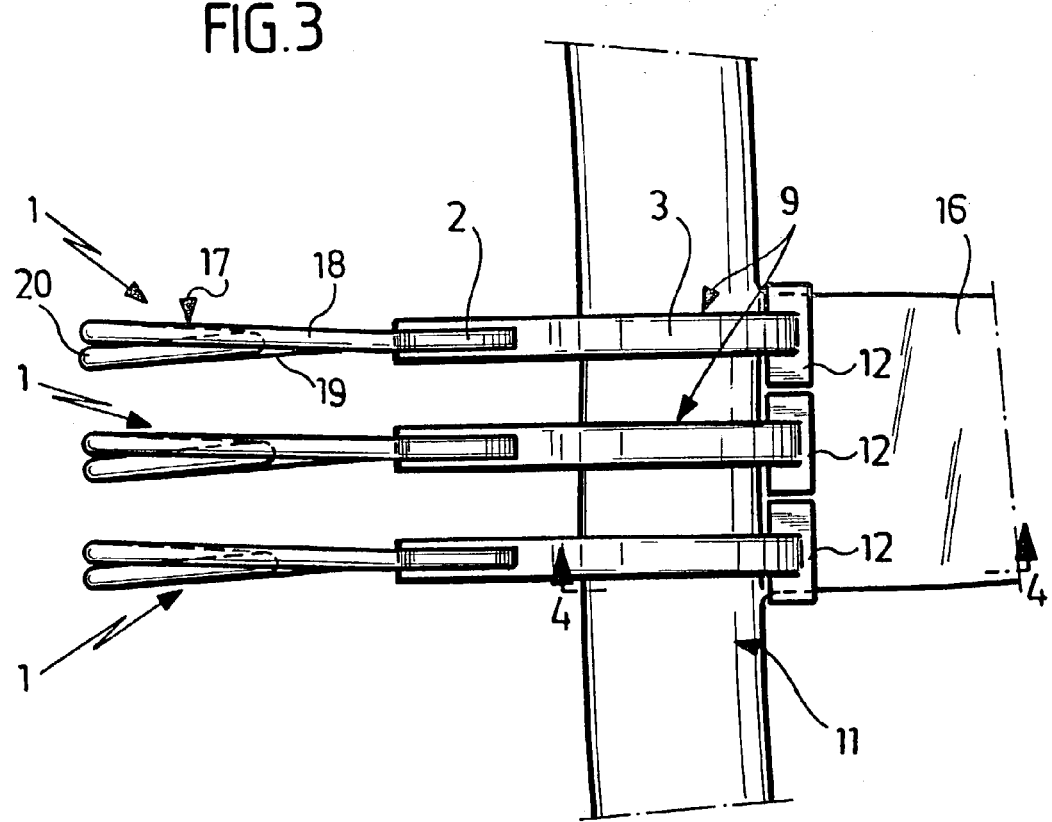
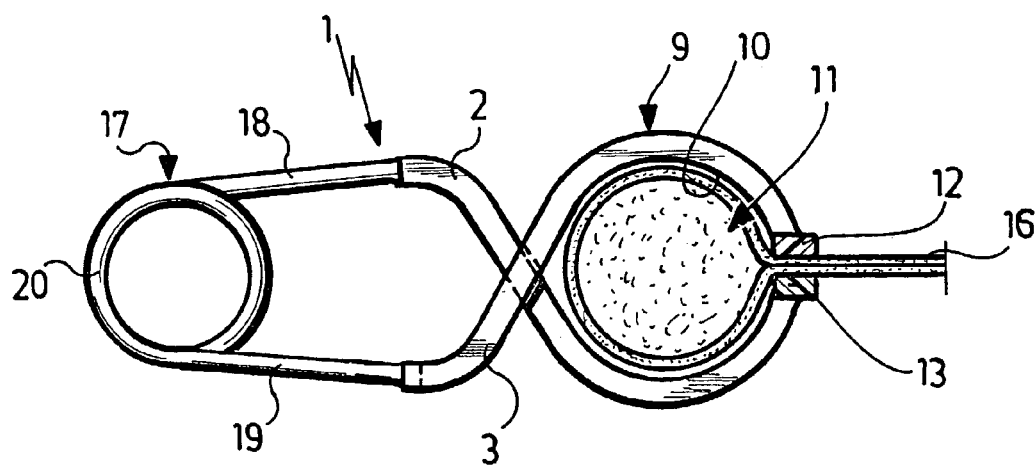

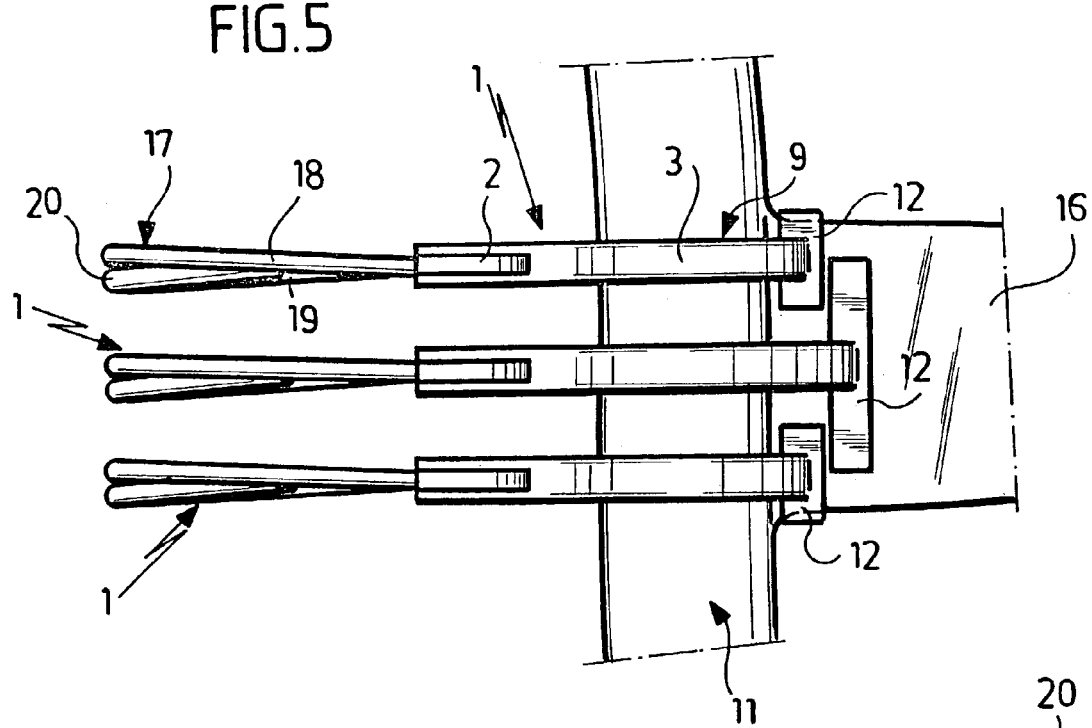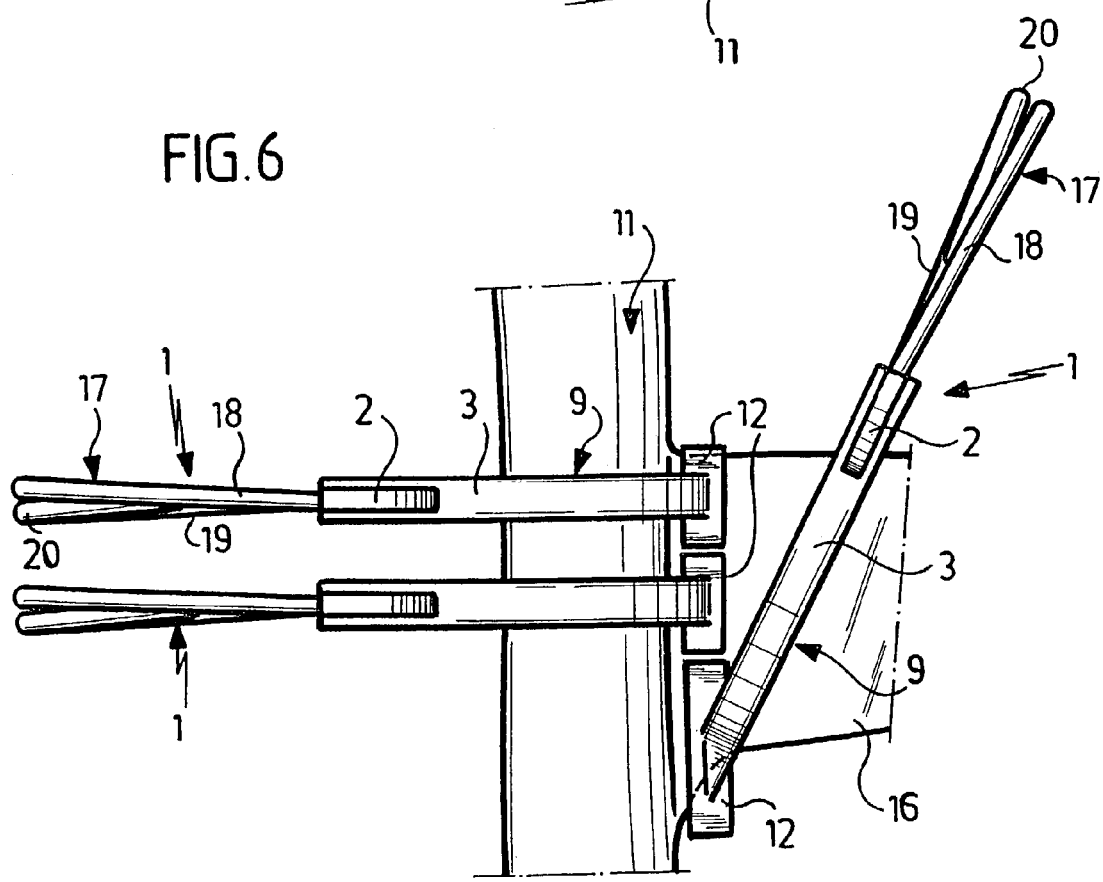

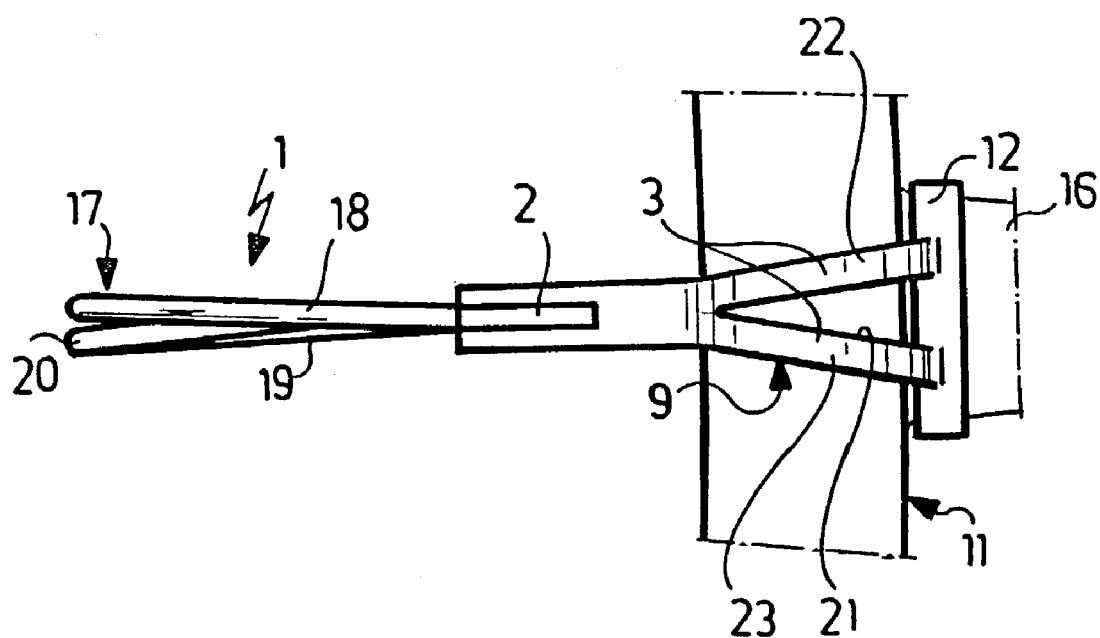

ANEURYSM CLIP

This application is a continuation of international application number PCT/US00/41200 filed on Oct. 17, 2000.

The invention relates to an aneurysm clip with two arms which are resiliently pivotable towards each other and carry at their free end clamping bars which are resiliently clamped against each other by the spring force of the arms, with outwardly curved sections of the arms adjoining the clamping bars and jointly forming a receiving space for a vessel.

Such aneurysm clips are known, for example, from EP 0 346 084 A1 or from U.S. Pat. No. 3,802,437.

In the clips of U.S. Pat. No. 3,802,437 outwardly curved sections whose width corresponds to the length of the clamping bars adjoin the relatively long clamping bars so as to produce a sleeve-shaped receiving space for a vessel. When several such aneurysm clips are applied alongside one another to a vessel, these outwardly curved, sleeve-shaped sections may impede one another and so it is not possible to place these clips in the desired manner close to one another.

In the aneurysm clip of EP 0 346 084 the clamping bars are bent laterally out of the center plane of the aneurysm clip to produce an asymmetrical arrangement, which involves the danger of the clips sliding down at one side. The one-sided stress on the clips by the bent clamping bars can result in canting and wedging, which can put the safety of the application of such an aneurysm clip at risk.

The object of the invention is to so improve a generic aneurysm clip that it enables, on the one hand, an unimpeded application, also of a plurality of clips, to a vessel, and, on the other hand, a particularly reliable sealing-off in the area of the clamping bars.

This object is accomplished with an aneurysm clip of the kind described at the outset, in accordance with the invention, in that the clamping bars protrude from the arms towards both sides and thereby project laterally on both sides over the width of the arms in the outwardly curved sections.

Such an aneurysm clip thus has relatively narrow arms in the area of the outwardly curved sections, but clamping bars which extend essentially transversely to the center plane of the aneurysm clip and project towards either side over the width of the arms are arranged at the end of the arms. The clamping bars are, therefore, supported on either side of the center plane of the aneurysm clip, and, at the same time, it is possible to place several aneurysm clips closely alongside one another because the arms are narrower than the clamping bars in the area of the outwardly curved sections surrounding the vessel. Therefore, several clips can be applied in such a way that their clamping bars overlap at the sides, while the arms are placed closely alongside one another in the outwardly curved sections. It is thus possible for the operator to apply several aneurysm clips to a vessel in such a way that a dividing line is ensured, possibly several times, and owing to the protruding of the clamping bars from the arms on either side, the aneurysm clips are optimally secured against canting and undesired twisting and therefore against sliding down.

Provision is made in a preferred embodiment for the clamping bars to be of straight-lined design in their longitudinal direction.

It is, however, also possible for the clamping bars to be bent in their longitudinal direction, and the arms can be arranged on the convex side of the clamping bars or on the concave side of the clamping bars so that the clamping bars are bent either away from the arms or towards the arms.

It is particularly advantageous for the clamping bars to be of symmetrical design in relation to the center plane of the aneurysm clip. The aneurysm clip can then be applied in the same way in both directions, and, in addition, the forces exerted on the clip by the symmetrical design are equal, which reliably prevents tilting and sliding down.

In particular, provision may be made for the clamping bars to extend in the area of connection to the arms at an angle of 90° to the center plane of the aneurysm clip.

However, in a special embodiment provision may also be made for the clamping bars to extend in the area of connection to the arms at an incline to the center plane of the aneurysm clip so that it is possible to arrange the arms such that they are at an incline in relation to the clamping line defined by the clamping bars.

In particular, the outwardly curved section can be of substantially circular design.

It is, however, also possible for the outwardly curved section to be oval design. This is expedient, particularly when the clamping bars extend at an incline to the center plane of the aneurysm clip because the outwardly curved section can then surround a vessel of substantially circular cross section when the arms also extend at an incline relative to the vessel.

The clamping bars can have a length which is between twice and eight times the width of the arms in the outwardly curved section. Clamping bars of different length can also be united in a set of such aneurysm clips.

The aneurysm clip can be of such design that the two arms are joined to each other by a resilient connecting section, for example, a single or multiple winding of a spring wire which continues in the two arms.

In another embodiment provision may be made for the two arms to be pivotally connected to each other and clamped against each other by a separate spring. In particular, this spring itself can form a bearing shaft for the pivot bearing of the two arms.

The arms connected to the clamping bars can have at least one opening in the area adjoining the clamping bars so that the arms are divided into two webs, each of which is connected to the clamping bars.

In particular, in this embodiment provision may be made for the arms in this area to be wider so that the webs extend in the shape of a V. Such a widening of the arms is also possible without provision of an opening.

Figure 8:
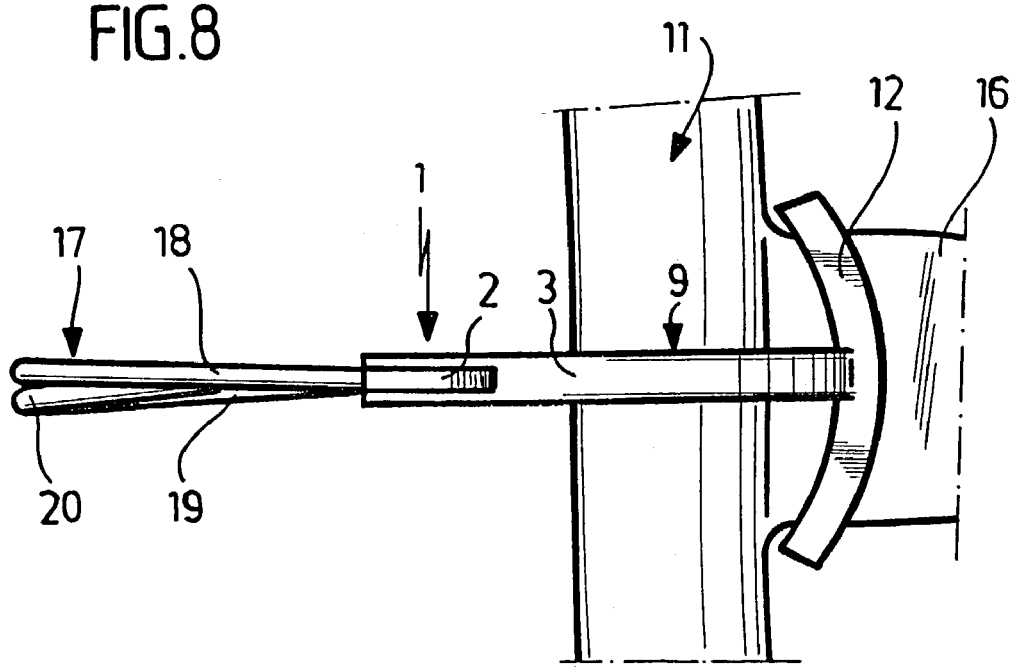

The following description of preferred embodiments of the invention serves in conjunction with the drawings to explain the invention in greater detail. The drawings show:

FIG. 1 a side view of a first preferred embodiment of an aneurysm clip applied to a vessel, and a straight-lined clamping bar which in comparison with the width of the clamping arms is long;

FIG. 2 a sectional view taken along 2—2 in FIG. 1;

FIG. 3 a view similar to FIG. 1 with three aneurysm clips applied alongside one another with short, straight-lined clamping bars and a resilient connecting section;

FIG. 4 a sectional view taken along 4—4 in FIG. 3;

FIG. 5 a view similar to FIG. 4 with aneurysm clips with clamping bars of different lengths applied in offset relation to one another;

FIG. 6 a view similar to FIG. 3 with two aneurysm clips with short, straight-lined clamping bars and an aneurysm clip with straight-lined clamping bars extending at an incline;

FIG. 7 a view similar to FIG. 3 with a single aneurysm clip with clamping bars bent away from the arms;

FIG. 8 a view similar to FIG. 7 with clamping bars bent towards the arms; and

FIG. 9 a view of a modified embodiment of an aneurysm clip similar to that of FIG. 5 with arms which widen in the shape of a V and have an opening.

The aneurysm clip 1 shown in FIGS. 1 and 2 comprises two arms 2, 3 made of a band-shaped material of rectangular cross section. At their rear end, both arms are bent in the shape of a circular arc and thus form a substantially circular bearing section 4 in which a helical spring 5 essentially consisting of two wound layers is located. This helical spring 5 abuts on the inner sides of the bearing section 4 and forms a bearing shaft which joins the two arms 2 and 3 in the area of the bearing section 4 for pivotal movement about the axis of the bearing section 4. The free ends 6, 7 of the helical spring 5 are supported on the outer side of the two arms 2, 3 immediately adjacent to the bearing section 4 on the latter and pivot the two arms 2 and 3 towards each other in such a way that they can only be pivoted apart elastically against the force of the helical spring 5.

Adjoining the bearing section 4 is a short intermediate section 8 in which the arms 2 and 3 extend parallel to each other and essentially abut on one another when the clip is closed.

This intermediate section 8 passes into a front vessel section 9 in which the two arms 2, 3 are outwardly bent in the shape of a semicircle and thus enclose a substantially circular receiving space 10 which receives a vessel 11 when the aneurysm clip is applied.

At their free ends, both arms 2, 3 are connected to straight-lined clamping bars which in the embodiment shown in FIGS. 1 and 2 extend parallel to the pivot axis of the two arms 2, 3, i.e., protrude vertically from the center plane of the aneurysm clip 1 towards both sides, more particularly, in the same way towards both sides, i.e., in the area of the clamping bars 12, 13 the aneurysm clip is of symmetrical design in relation to its center plane. The clamping bars 12, 13 are located directly opposite each other and are pressed against each other by the helical spring 5 in the closed state such that they abut on one another throughout their entire length.

In the embodiment shown in FIGS. 1 and 2, the length of the clamping bars 12, 13 in their longitudinal direction is approximately eight times greater than the width of the arms 2, 3 in the area of the receiving space 10.

To apply the aneurysm clip 1 illustrated in FIGS. 1 and 2, the arms 2 and 3 are pivoted outwards against the force of the helical spring 5, for example, by pressure on projections 14, 15 protruding radially at the rear ends of the arms 2, 3 so that the clamping bars 12 and 13 can be guided past a vessel 11 until the vessel 11 is located in the area of the receiving space 10 in the vessel section 9. When closing the aneurysm clip 1, the arms 2 and 3 are pivoted towards each other under the action of the helical spring 5, and the clamping bars 12, 13 position themselves at vessel walls 16 of a protuberance or an aneurysm protruding at the sides from the vessel 11 and thus close off this protuberance towards the vessel 11 over the entire width thereof. One aneurysm clip 1 of the described kind is thus sufficient to close off a protuberance over quite a large area in essentially the shape of a line. Owing to the relatively large length of the clamping bars 12, 13, this length is substantially greater than the width of the arms 2, 3 and thus also the width of the aneurysm clip 1 in a direction perpendicular to the center plane.

A similar arrangement is shown in the embodiment of FIGS. 3 and 4, and, therefore, corresponding parts bear the same reference numerals.

Differently from the embodiment of FIGS. 1 and 2, the arms 2 and 3 of this embodiment are not pivotally joined to each other in the area of a bearing section 4 by a helical spring 5, but instead the two arms 2 and 3 are joined to each other by an elastic connecting section 17 having two legs 18 and 19, which are each joined to one of the arms 2 and 3, respectively, and are joined together by an elastic web 20 so that the legs 18 and 19 are elastically bendable apart owing to the inherent elasticity of the web. In the area of the web 20, the material of the connecting section 17 can be formed through 360° on itself in the form of an eyelet or helix so as to produce an elastic coil by means of which the inherent elasticity in the area of the web 20 can be increased. It is preferable for the arms 2 and 3 and the connecting section 17 to be integrally made from an elastic material, for example, from spring wire, but it is also possible for the connecting section 17 to be joined to arms made of a different material, for example, the arms 2, 3 can consist of a sterilizable plastic material and be joined to legs 18 and 19 made of spring wire.

In the embodiment of FIGS. 3 and 4, the arms 2 and 3 also form a vessel section 9 with clamping bars 12, 13 arranged at the front end thereof. However, in the embodiment of FIGS. 3 and 4 these are significantly shorter than in the embodiment of FIG. 1, the length of the clamping bars in this embodiment being only approximately three times the width of the arms 2, 3.

It is thereby possible to arrange several such aneurysm clips 1 directly alongside one another on a vessel 11 in the area of the vessel wall 16 bulging out at the side so that a line-shaped clamping is also achieved, but using three aneurysm clips 1 and thus employing a higher clamping force since each aneurysm clip 1 exerts its inherent clamping force on a shorter clamping bar 12, 13.

It is, of course, also possible to use aneurysm clips 1 with correspondingly short clamping bars, which like the aneurysm clip 1 of FIGS. 1 and 2 do not have an elastic connecting section 17 at their disposal, but a bearing section 4 with a helical spring 5.

Aneurysm clips 1 which are of essentially the same construction as in the embodiment of FIG. 3 are used in the embodiment of FIG. 5. Aneurysm clips whose clamping bars 12, 13 are of different length are used at only one point of application. In addition, the dimensions of the aneurysm clips 1 and 2 in the longitudinal direction are selected so as to differ, and so, for example, the center aneurysm clip 1 of FIG. 5 is of somewhat longer construction than the two aneurysm clips 1 at the sides. The clamping bars 12, 13 of the three aneurysm clips 1 can thus be arranged at a different spacing from the vessel 11. An overlapping of neighboring clamping bars 12, 13 is, therefore, possible, and a particularly effective closure of the vessel wall 16 of a lateral protuberance is thereby achieved. The different length is, for example, achievable by the vessel section 9 in the case of the longer aneurysm clip 1 not—as in the case of the other aneurysm clips 1—surrounding a circular area, but an oval area which is elongate in the longitudinal direction.

The aneurysm clips shown in FIG. 6 correspond to those of FIG. 3, and corresponding parts bear the same reference numerals.

In the embodiment of FIG. 6, one of the three aneurysm clips arranged alongside one another is replaced by an aneurysm clip on which the clamping bars 12, 13 extend at an incline to the longitudinal direction of the arms 2, 3, i.e., at an incline to the center plane of the aneurysm clip 1. Also, in this embodiment of the aneurysm clip 1 an oval vessel section 9 is likewise effected, with its long axis running in the longitudinal direction of the aneurysm clip 1.

It is thus possible to apply this aneurysm clip 1 to the vessel 11, also from the side opposite the vessel 11, such that the vessel wall 16 is clamped off in continuation of the clamping bars 12, 13 of the two other aneurysm clips 1, with this aneurysm clip 1 then not surrounding the vessel 11, but the vessel wall 16 of the protuberance.

The aneurysm clips of FIGS. 7 and 8 correspond fully to those of FIG. 3, with the difference that the clamping bars 12, 13 are not of straight-lined construction, but have the shape of a circular arc. In the embodiment of FIG. 7 the arms 2, 3 are located on the convex side of the arcuate clamping bars 12, 13, in the embodiment of FIG. 8 on the concave side. In both cases, the construction of the clamping bars 12, 13 is symmetrical in relation to the center plane, and clamping bars 12, 13 located opposite each other are, of course, of the same design so that the clamping surfaces of these clamping bars 12, 13 lie opposite each other throughout their entire surface during the closing.

A further preferred embodiment of an aneurysm clip which corresponds substantially to the constructions shown in FIG. 5 is shown in FIG. 9. In this embodiment, the arms 2, 3 are widened in the area adjoining the clamping, bars 12, 13 and have an opening 21 so that the arms 2, 3 extend in the form of two webs 22 and 23 arranged in the shape of a V and opening into the clamping bars 12, 13.

What is claimed is:

1. Aneurysm clip comprising:
   two arms joined at one end by a spring, said arms being pivotable towards each other about a pivot axis and carrying at respective free ends thereof clamping bars which, in a rest position, are resiliently held against each other by a spring force exerted by said spring;
   outwardly curved sections of the arms which precede said free ends forming a space for receiving a vessel portion that is not to be clamped;
   the clamping bars protruding parallel to said pivot axis and laterally away in opposite directions from first and second opposite sides of each of the outwardly curved sections, and being curved to provide one of a convex and a concave shape adapted to clamp an aneurysm;
   the respective positions of said space and said clamping bars allowing a protuberance of a vessel to be clamped by said bars when said vessel portion is received in said space without being clamped.

2. Aneurysm clip as defined in claim 1, wherein the clamping bars are curved in their longitudinal direction.

3. Aneurysm clip as defined in claim 2, wherein the arms are arranged on a convex side of the clamping bars.

4. Aneurysm clip as defined in claim 2, wherein the arms are arranged on a concave side of the clamping bars.

5. Aneurysm clip as defined in claim 2, wherein the clamping bars are of symmetrical design in relation to a center plane of the aneurysm clip.

6. Aneurysm clip as defined in claim 1, wherein the clamping bars are of symmetrical design in relation to a center plane of the aneurysm clip.

7. Aneurysm clip as defined in claim 6, wherein the outwardly curved sections are of substantially circular design.

8. Aneurysm clip as defined in claim 6, wherein the outwardly curved sections are of oval design.

9. Aneurysm clip as defined in claim 6, wherein the clamping bars have a length which is between twice and ten times the width of the arms in the outwardly curved sections.

10. Aneurysm clip as defined in claim 6, wherein in the area of connection to the arms the clamping bars extend at an angle of 90° to the center plane of the aneurysm clip.

11. Aneurysm clip as defined in claim 1, wherein in the area of connection to the arms, the clamping bars extend at an incline to a center plane of the aneurysm clip.

12. Aneurysm clip as defined in claim 11, wherein the outwardly curved sections are of substantially circular design.

13. Aneurysm clip as defined in claim 11, wherein the outwardly curved sections are of oval design.

14. Aneurysm clip as defined in claim 11, wherein the clamping bars have a length which is between twice and ten times the width of the arms in the outwardly curved sections.

15. Aneurysm clip as defined in claim 1, wherein the outwardly curved sections are of substantially circular design.

16. Aneurysm clip as defined in claim 1, wherein the outwardly curved sections are of oval design.

17. Aneurysm clip as defined in claim 1, wherein the clamping bars have a length which is between twice and ten times the width of the arms in the outwardly curved sections.

18. Aneurysm clip as defined in claim 17, wherein the clamping bars are of symmetrical design in relation to a center plane of the aneurysm clip.

19. Aneurysm clip as defined in claim 1, wherein the spring itself forms a bearing shaft for the pivot bearing of the two arms.

20. Aneurysm clip as defined in claim 1, wherein in the area of connection to the arms the clamping bars extend at an angle of 90° to a center plane of the aneurysm clip.

21. Aneurysm clip as defined in claim 20, wherein the outwardly curved sections are of substantially circular design.

22. Aneurysm clip as defined in claim 20, wherein the clamping bars have a length which is between twice and ten times the width of the arms in the outwardly curved sections.

23. Aneurysm clip as defined in claim 1, wherein the pivotable arms have an opening in the area in which they adjoin the clamping bars.

24. Aneurysm clip as defined in claim 1, wherein the arms widen towards the clamping bars in the area in which they adjoin the clamping bars.

* * * * *